(12) United States Patent
Majeed et al.

(10) Patent No.: US 8,987,212 B2
(45) Date of Patent: *Mar. 24, 2015

(54) OLEANOYL PEPTIDE COMPOSITION AND METHOD OF TREATING SKIN AGING

(76) Inventors: Muhammed Majeed, East Windsor, NJ (US); Kalyanam Nagabhushanam, East Windsor, NJ (US); Renukeshwar H Chandramouli, Bangalore (IN); Rattan Sood, Bangalore (IN); Subbalakshmi Prakash, East Windsor, NJ (US); Susmitha Anand Tathapudi, Bangalore (IN)

( * ) Notice: Subject to any disclaimer, the term of this patent is extended or adjusted under 35 U.S.C. 154(b) by 339 days.

This patent is subject to a terminal disclaimer.

(21) Appl. No.: 12/979,667

(22) Filed: Dec. 28, 2010

(65) Prior Publication Data
US 2011/0091398 A1   Apr. 21, 2011

Related U.S. Application Data

(63) Continuation-in-part of application No. 11/835,165, filed on Aug. 7, 2007.

(51) Int. Cl.
*A61K 38/08* (2006.01)
*A61K 8/64* (2006.01)
*A61Q 19/00* (2006.01)
*A61Q 19/08* (2006.01)
*C07K 7/06* (2006.01)

(52) U.S. Cl.
CPC . *A61K 8/64* (2013.01); *A61Q 19/00* (2013.01); *A61Q 19/08* (2013.01); *C07K 7/06* (2013.01)
USPC ........................ 514/21.8; 514/18.6

(58) Field of Classification Search
None
See application file for complete search history.

(56) References Cited

U.S. PATENT DOCUMENTS

| 6,620,419 B1 * | 9/2003 | Lintner ......................... 424/401 |
| 2009/0169651 A1 * | 7/2009 | Majeed ........................ 424/727 |
| 2010/0034758 A1 * | 2/2010 | Majeed et al. .................. 424/59 |

OTHER PUBLICATIONS

Definition of derivative retrieved from http://www.chemicool.com/definition/derivative.html on May 16, 2012 1 page.*
Kohl et al ('Skin aging' J Eur Acad Dermatol Veneril v25(8) 2011, abstract only retrieved from http://www.ncbi.nlm.nih.gov/pubmed/21261751 on Jun. 30, 2014, 2 pages).*
Olshansky et al ('No truth to the fountain of youth' Scientific American Monday Dec. 29, 2008, retrieved from http://www.scientificamerican.com/article.cfm?id=no-truth-to-the-fountain-of-youth&pri on Dec. 16, 2013, 4 pages).*
Lu et al ('The extracellular matrix: a dynamic niche in cancer progression' The Journal of Cell Biology v196(4) 2012 pp. 395-406).*
The Clinique (retrieved from http://www.theclinique.net/procedures/face/infini/ on Jun. 30, 2014, 7 pages).*

* cited by examiner

*Primary Examiner* — James H Alstrum Acevedo
*Assistant Examiner* — Ronald Niebauer

(57) ABSTRACT

The present invention relates to a composition containing peptide of SEQ ID NO: 1 linked to oleanolic acid and a method of treating skin aging. The composition effectively reduces signs of ageing due to oxidation, collagen insufficiency and excess activity of serine proteases like elastase and collagenase that result in wrinkling of skin, fine expression lines, reduced skin thickness, hyperpigmentation, under eye dark circles, and premature ageing.

1 Claim, 16 Drawing Sheets

(a)

(b)

(a)

(b)

(a)

(b)

(a)

(b)

(a)

(b)

(c)

(d)

(a)

(b)

(c)

(e)

(f)

(g)

(h)

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence : Synthetic
      peptide

<400> SEQUENCE: 1

Lys Thr Thr Lys Ser
1               5
```

OLEANOYL PEPTIDE COMPOSITION AND METHOD OF TREATING SKIN AGING

Figure 1:
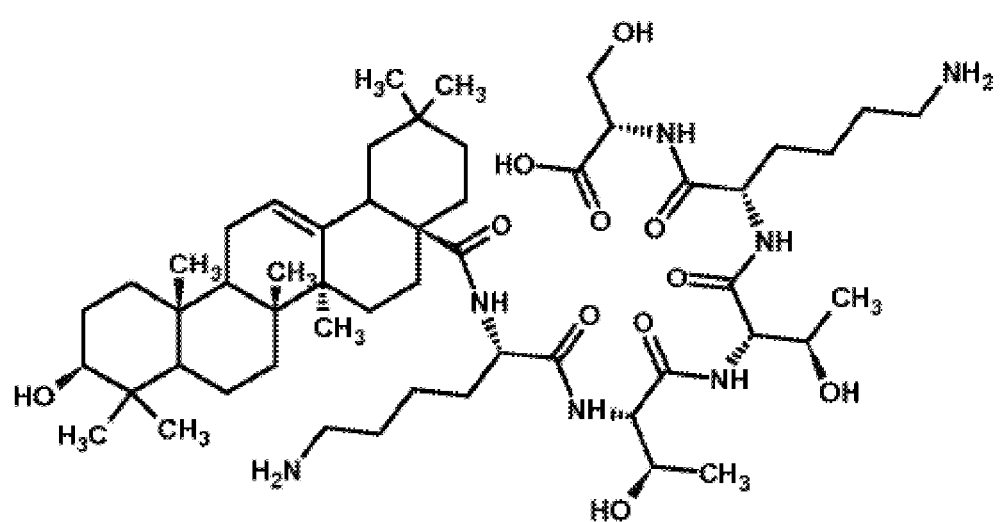

This application is a continuation-in-part of application Ser. No. 11/835,165 filed Aug. 7, 2007 titled "Peptides modified with triterpenoids and Small Organic molecules: Synthesis and Use in Cosmeceuticals" which is hereby incorporated by reference in their entirety for all purposes.

FIELD OF THE INVENTION

The present invention relates to a composition containing peptide of SEQ ID NO: 1 linked to oleanolic acid and its use in treating skin aging. The peptide of SEQ ID NO: 1 linked to oleanolic acid is present in the composition either individually or in combination with ingredients or plant extracts selected from a group comprising coconut liquid endosperm, amla extract, stilbenes or its derivatives, tetrahydrocurcuminoids or its derivatives and licorice extract. The composition effectively reduces ageing due to oxidation, collagen insufficiency and excess activity of serine proteases like elastase and collagenase that result in wrinkling of skin, fine expression lines, reduced skin thickness, hyperpigmentation, under eye dark circles, and premature ageing.

BACKGROUND OF THE INVENTION

The appearance and condition of the skin may be degraded through the effects of environmental factors, either naturally occurring (sunlight, wind abrasion, humidity, etc) or manmade (heating, air condition, pollutants, etc.), pathological processes such as dermatological diseases or the normal aging process. The various insults to which the skin is exposed may act individually or synergistically. To ameliorate or prevent the deterioration of skin quality that may occur over time, consumers have increasingly sought new or improved cosmetic compositions and cosmetic methods for skin care. Such products or methods prevent, delay or reverse the visible signs of the aging process, such as the appearance of wrinkles, lines, loss of skin tone, thinning of the skin, hyper pigmentation or mottling and age spots. Such products or methods improve the appearance and condition of sensitive, dry or flaky skin, and/or soothe skin that has been irritated by exposure to chemicals, wind, or sunlight, among other potential irritants.

With an aging population, there has been an increase in the study of aging as it relates to the human body and, more particularly, human skin. For example, treatment of aging skin exhibited by the presence of fine lines, wrinkles and the like has received a great deal of attention. The dermal signs of aging such as fine lines, wrinkles, laxity, and hyperpigmentation have been fought through many tactics including surgery, laser treatment and cosmetics. Cosmetic treatments include use of various creams and lotions to alter the effects of dermal aging. Much of the literature in the prior art focuses on the use of a single primary component to prevent one of several deleterious aging affects. For example, one tactic has been to use one or more hydroxy acids or retinoic acid to stimulate the re-growth of dermal cells without other components. This approach is flawed because it does not recognize that aging is caused by the deleterious interaction of multiple agents on the skin, from multiple sources, causing damage to the skin through multiple simultaneous damage pathways.

Consumers are increasingly seeking "anti-aging" products that treat wrinkling, creasing and furrowing of the skin. The advent of costly and painful cosmetic injections for treating expression lines of the face has heightened interest in finding topical alternatives that are effective and non-invasive.

Expression lines are a distinct type of wrinkle that occurs on the facial skin at an early adult age. They are related anatomically to the facial expression muscles in the periorbital, glabella, forehead and perioral areas. The activity of these muscles during the actions of smiling, squinting, pursing of the lips and frowning places greater physical stress upon the overlying skin than in other areas in the face. For this reason, expression lines are less responsive to those topical treatments that focus upon the non-contractile elements of cutaneous anatomy, such as the epidermis. In order to be most effective, treatment of expression lines should also entail the inhibition of the facial expression muscles and the muscle fiber elements associated with the dermis. A myriad of substances that relax striated muscle fibers are described in the cosmetic prior art. The problem is that the muscle relaxants of the prior art are either slow acting, not potent enough or the inhibitory effects are not cumulative. Furthermore, none of these muscle relaxants reduce facial muscle actions. A newly discovered plant extract that rapidly inhibits deformation of the dermis enables substances that repair and rejuvenate it to become more effective.

An expression line is formed when a muscle of facial expression contracts or shortens itself beneath the skin and then relaxes and returns to its resting length. The skin can also shorten and rebound, but not as well as the muscle. Therefore, the skin tends to buckle and fold inward as the muscle contracts. The ability of the skin to withstand the shortening and rebounding of the underlying muscle is related to the quality and health of the upper dermis. With increasing age, the thickness, elasticity, collagen content and reparative ability of the dermis diminishes. The skin can no longer rebound from this action and the fibrous intercellular matrix of the dermis weakens and breaks. At this point, the skin has developed a permanent wrinkle. The wrinkle will continue to deepen as this area of the skin is subjected to the perpetual stress of facial expressions.

Anatomy of Expression lines

The skin associated with expression lines is different histologically from that found elsewhere in the face. The interlobular septa of the sub-dermal connective tissue contains striated muscle tissue fibers (panniculus carnosus). These fibers arise from the underlying facial muscle groups. They are integrated within the collagenous network of the lower (reticular) dermis. A sub-population of dermal fibroblasts in the upper (papillary) dermis, known as "myo-fibroblasts", have inherent contractile characteristics similar to striated muscle tissue. Contractions within these dermal fibroblasts are mediated by the same neurotransmitter, i.e. acetylcholine, as the fiber elements of striated muscle.

Muscle fibers within the facial skin have a direct influence on its surface smoothness and modulating the neural motor influx to these muscle fibers causes a reduction of wrinkles. For example, patients who suffer from Bell's palsy of the facial nerve have smoother skin on the paralyzed side of the face than on the non-paralyzed side. Also, Botox.™ Cosmetic injections not only immobilize the forehead and upper eyebrow muscles, but also smoothen the skin external to these muscles. Botox.™ interferes with the uptake of acetylcholine within the synaptic junction of the afferent motor neuron of muscle fibers, thereby preventing contraction of muscle tissue associated with wrinkles and furrows. Botox.™ treatment is in high demand and thus, it is the goal of cosmetic scientists to develop a topical equivalency (see A. Blitzer et al., Arch.

Otolaryngol. Head Neck Surg., 119, pages 1018 to 1022 (1993)) (see J. D. Carruthers et al., J. Dermatol. Surg. Oncol., 18, pages 17 to 21 (1992).

To meet consumer demand, many cosmetic compositions and cosmetic methods have been developed for skin care and treatment. However, many, if not most, of the products or treatment methods described to date lead to inadequate results or are marred by undesirable side effects. These may include irritation of the skin or adjacent mucous membranes, the production of excessive oiliness or greasiness of the skin or discoloration of the skin.

Dermal Repair: The regenerative ability of the dermis has a critical bearing on its ability to withstand the chronic muscle contraction and relaxation of the expressive muscles. As a consequence of aging or sun damaged skin, there is a reduction in the fibroblastic cells and blood vessels that are needed to rejuvenate the lower dermis. Fibroblasts in the "basal layer" of the upper dermis replicate into new cells more slowly, loose their capacity to manufacture collagen and are less able to organize and preserve the collagen fiber network. Since the dermal matrix is the source of collagen and major water holding molecules, i.e. the glycoaminoglycans and hyaluronic acid, preserving it is essential to the health of the epidermis. Without continual replenishment of precursor proteins, disorganization and dissolution of the collagen fiber network and the extra-cellular matrix takes place. The result of this process is a flattening of the dermal-epidermal junction and a weakening of the mechanical resistance of the upper dermis. Thus, the aging skin has a much greater susceptibility for temporary deformations—that occur during facial expression—to become permanent. (see Oikarinen, "The Aging of Skin: Chronoaging Versus Photoaging," Photodermatol. Photoimmunol. Formation, Photomed., vol. 7, pp. 3-4, 1990). (see Thalmann et al. "A Computational Skin Model: Fold and Wrinkle Formation" pp. 1-5).

There are several teachings in the art (U.S. Pat. No. 6,794,362) (U.S. Pat. No. 6,777,389) that discuss singular molecules or compositions thereof for enhancing the elasticity of skin or strengthening the dermis. They are formulated from peptides or peptide-like compounds that mimic the molecular composition of elastin or add to it. Mitts et al. (U.S. Pat. No. 6,809,075) postulated that a peptide/retinoid composition could integrate within the elastin component of the dermis, thereby increasing the ability of the skin to rebound from deformation. More often, the prior art teaches that natural or synthetic peptide formulations can enhance the collagen fiber network or extra-cellular substrate of the dermal matrix. Lowe, N. et al., (Pharmacology of Retinols In Skin", Vol. 3 (1989), pp. 240-248) emphasize the role of retinoids in maintaining the structural integrity of skin. However, the instability and irritation caused by retinoids are problematic. Approach advocated by Dioguardi (U.S. Pat. No. 5,198,465) is to increase the collagen content in the skin in general by the topical application of synthesized precursor collagen molecules and coenzymes of the collagen metabolic pathway. The premise is that direct replacement via diffusion and adsorption of precursor molecules fortifies deficient skin. A similar notion taught by Kludas (U.S. Pat. No. 5,055,298) is that a substantially natural composition can have a reparative and remodeling effect at the dermal-epidermal junction. Also, recent art (U.S. Pat. No. 6,906,036, U.S. Pat. No. 6,884,425) has taught that inhibitors of matrix metalloprotienases are capable of preventing the disruption of the dermis, healing it and facilitating a return to normal healthy skin. None of the aforementioned patents teach the capacity to stimulate fibroblastic activity and synthesis of collagen precursors; nor do they profess to restore dermal thickness and collagen fiber network.

In a recent patent, Varani, et al. (U.S. Pat. No. 6,919,072) identifies a composition of a retinoid and a matrix metalloproteinase inhibitor that inhibits collagen breakdown, promotes collagen at the content by increasing procollagen synthesis, increases keratinocytes and fibroblastic proliferation. The invention restores the thickness of the epidermal-dermal interface in chronologically aged skin and it restores collagen content within the upper dermis to normal levels. Therein lies its property to give the skin strength to withstand environmental and physical stress. As with other retinoids, the retinoid of Lowe requires prolonged application and the dermal repair is much slower than with the preferred embodiment of this application.

The Significance of Peptides

The focus of the early art has been on disclosing substances that were thought to physically replenish the molecules that build new collagen or that add substances which irritate or disrupt the basal layer to effect its regeneration and healthy reconstitution. More recent art teaches the benefits of topical peptide treatments in stimulating the upper dermis to renew itself by cellular re-growth. This is supported by the knowledge that the body has naturally occurring peptides that are instrumental in stimulating the healing process following a wound to the skin. Robinson teaches (U.S. Pat. No. 6,492,326) various formulations containing combinations of palmitoyl pentapeptide-3, derivatives of pentapeptides and mixtures thereof. Lintner (U.S. Pat. No. 6,620,419) discloses peptide formulas of the general sequence palmitoyl-lysyl-threonyl-threonyl-lysyl-serine (palmitoyl group attached to SEQ ID NO: 1) that increase the synthesis of collagen and glylcosaminoglycans. They act synergistically to heal wrinkles and other forms of skin aging far more effectively than earlier formulations. The key difference in the Lintner teaching to that of Robinson is the addition of a fatty acid chain onto the terminal end of a pentapeptide that makes this lipophilic modified peptide very efficient at penetrating the epidermis and thus more effective in reaching the formative layers of the dermis. The net result is to increase the thickness of the skin by restoring the reparative capacity of the upper dermis. Consequently, the skin is better able to withstand the deformation imposed on it by the active contraction and relaxation of expression muscles and micro-contractions within the skin itself.

More comprehensive studies have found that environmental factors, such as stress, sun exposure and impurities in food, water and air also adversely affect components of the epidermal and dermal layers of the skin which, in turn, impact and alter the appearance of the skin and lead to an appearance of premature aging. For example, factors such as free radicals, reactive nitrogen species ("RNS"), reactive oxygen species ("ROS") and other oxidizing species ("OOS") can adversely impact the human body including the skin. Particular factors within the groups noted above that have been found to impact and adversely affect the appearance of the skin include nitric oxide, superoxide radicals, hydrogen peroxide and hydroxide free radicals. These factors have been variously implicated in a number of skin conditions including photodamage, general aging of the skin, contact dermatitis, wrinkling, lipid peroxidation, enzyme degradation, reduction and breakdown of collagen and/or elastin, degradation and inhibited reproduction of DNA, inflammation and general damage to the skin tissue.

Antioxidant activity is an activity that reduces production of reactive oxygen species in the body and at the same time, prevents oxidation that causes irrecoverable damages to cells.

Ground-state or triplet oxygen can be activated as a result of exposure to environmental or biochemical factors such as enzymes, reduction metabolism, chemical compounds, pollutants and photochemical reactions, and transformed into reactive oxygen species (ROS) which have a high reactivity such as superoxide radicals, hydroxy radicals and hydrogen peroxide. Accordingly, it results in irreversibly disrupting cell constituents. The actions of such reactive oxygen species can be reduced by antioxidant enzymes such as superoxide dismutase (SOD), catalase and peroxidase and antioxidant substances such as vitamin C, vitamin E and glutathione, which all form the body's defense system. However, where disorder of such a defense mechanism in the body or exposure to excessive reactive oxygen species occurs, reactive oxygen species may irreversibly disrupt lipid, protein and DNA. Various diseases inclusive of aging, cancer, multiple arteriosclerosis, arthritis and Parkinson's disease are the result.

Synthetic antioxidants such as BHA (butylated hydroxy anisole), BHT (butylated hydroxy toluene) and NDGA (nordihydro-guaiaretic acid) have been developed to date. By way of examples of natural antioxidants, there are antioxidant enzymes such as superoxide dismutase, peroxidase, catalase and glutathione peroxidase, and non-enzymatic antioxidant substances such as tocopherol (vitamin E), ascorbic acid (vitamin C), carotenoid and glutathione.

However, synthetic antioxidants may cause allergic reactions and oncogenesis due to their strong toxicity in the body, and are easily disrupted by heat due to temperature sensitivity. On the other hand, natural antioxidants are safer than synthetic antioxidants in the body but have the problem of weaker effect. Therefore, the development of a new natural antioxidant having no problem with safety in use and also having excellent antioxidant activity is required. Topically-applied antioxidants do have merit for all skin types to keep skin healthy and help prevent sun damage and improve cell function.

Antioxidants have been conclusively shown to exert a positive effect on reducing skin irritation and inflammation, and that is a crucial step in creating or maintaining healthy, vibrant skin and, therefore potentially reducing wrinkles. (International Journal of Experimental Pathology, 2000:257-263; Skin Pharmacology and Applied Skin Physiology, 2000: 143-149)

Several hundred molecules having a polyphenol (polyhydroxyphenol) structure (i.e. several hydroxyl groups on aromatic rings) have been identified in edible plants. These molecules are secondary metabolites of plants and are generally involved in defense against ultraviolet radiation or aggression by pathogens. Polyphenols are widespread constituents of fruits, vegetables, cereals, dry legumes, chocolate, and beverages such as tea, coffee or wine.

These compounds may be classified into different groups as a function of the number of phenol rings that they contain and of the structural elements that bind these rings to one another. Classes of polyphenols include the phenolic acids, flavonoids, stilbenes and lignans. There are two classes of phenolic acids: derivatives of benzoic acid and derivatives of cinnamic acid.

It is indeed not practical to measure each and every one of the antioxidants in vivo. It is also now widely hypothesized that the major factor influencing oxidative stress is the overall antioxidant status of the system, which prevents diseases by eliminating free radicals and ROS. Therefore, it is essential to have a method capable of measuring collectively the extracellular antioxidant status. There are methods for measuring antioxidant status which are based on the inhibition of generated free radicals reaching the target indicator molecules, by antioxidants. The common feature for inhibition assays is to generate a free radical to react with a target molecule, thereby generating an endpoint that can be observed and quantified. Addition of antioxidants inhibits the development of this endpoint. A good example of this is the DPPH (1,1-diphenyl-2-hydrazyl) free radical scavenging activity.

Elastin, found in highest concentrations in the elastic fibers of connective tissues, is responsible for the texture and tone of the skin. ELASTASE, a serine protease enzyme, has a role in dissociating tissues which contain extensive intercellular fiber networks. Excess elastase production will result in wrinkling of skin/premature ageing.

The vital protein, collagen, maintains the skin tone and structure. COLLAGENASE is a serine protease enzyme that cleans the wound of any dead tissue leaving the wound bed ready for healing. Collagenase, intensely produced during inflammation, is known to have role in Skin wrinkling by digesting the vital protein collagen that maintains the skin tone and structure.

Another mechanism for Anti ageing is collagen enhancement in the skin. Actives that can physically replenish the molecules that build new collagen or that adds substances which irritate or disrupt the basal layer to effect its regeneration and healthy reconstitution are excellent for Anti ageing compositions. More recent art teaches the benefits of topical peptide treatments in stimulating the upper dermis to renew itself by cellular re-growth. This is supported by the knowledge that the body has naturally occurring peptides that are instrumental in stimulating the healing process following a wound to the skin. Robinson teaches (U.S. Pat. No. 6,492, 326) various formulations containing palmitoyl pentapeptide-3, derivatives of pentapeptides, and mixtures thereof. Lintner (U.S. Pat. No. 6,620,419) discloses peptide formulas of the general sequence palmitoyl-lysyl-threonyl-lysyl-serine (Palmitoyl group attached to SEQ ID NO: 1) that increase the synthesis of collagen and glylcosaminoglycans. They act synergistically to heal wrinkles and other forms of skin aging far more effectively than earlier formulations.

The present invention discloses composition containing peptide of SEQ ID NO: 1 linked to oleanolic acid and its effective use in treating skin aging

SUMMARY OF THE INVENTION

The present invention provides a composition containing peptide of SEQ ID NO: 1 linked to oleanolic acid and a method of treating skin aging. The composition effectively acts by multiple mechanisms in preventing, delaying and/or reversing skin aging caused by loss of skin elasticity, collagen deformation, inflammation, free radical induced skin damage etc The peptide of SEQ ID NO: 1 linked to oleanolic acid is present in the composition either individually or in combination with ingredients or plant extracts. The composition containing peptide of SEQ ID NO: 1 linked to oleanolic acid and ingredients or plant extracts shows synergistic effect in treating specific signs of skin aging. The ingredients or plant extracts are selected from a group comprising coconut liquid endosperm, amla extract, stilbenes or its derivatives, tetrahydrocurcuminoids or its derivatives, licorice extract and combinations thereof. Stilbenes are selected from a group comprising oxyresveratrol, pterostilbene, resveratrol, 3-hydroxypterostilbene and combinations thereof.

The concentration of Oleanoyl peptide used in the invention ranges from about 0.0001 to about 10%.

The concentration of ingredients or plant extracts used in the composition ranges from about 0.0001 to about 10%.

BRIEF DESCRIPTION OF ACCOMPANYING FIGURES

FIG. 1: Structure of peptide of SEQ ID NO: 1 linked to oleanolic acid.

Figure 2:
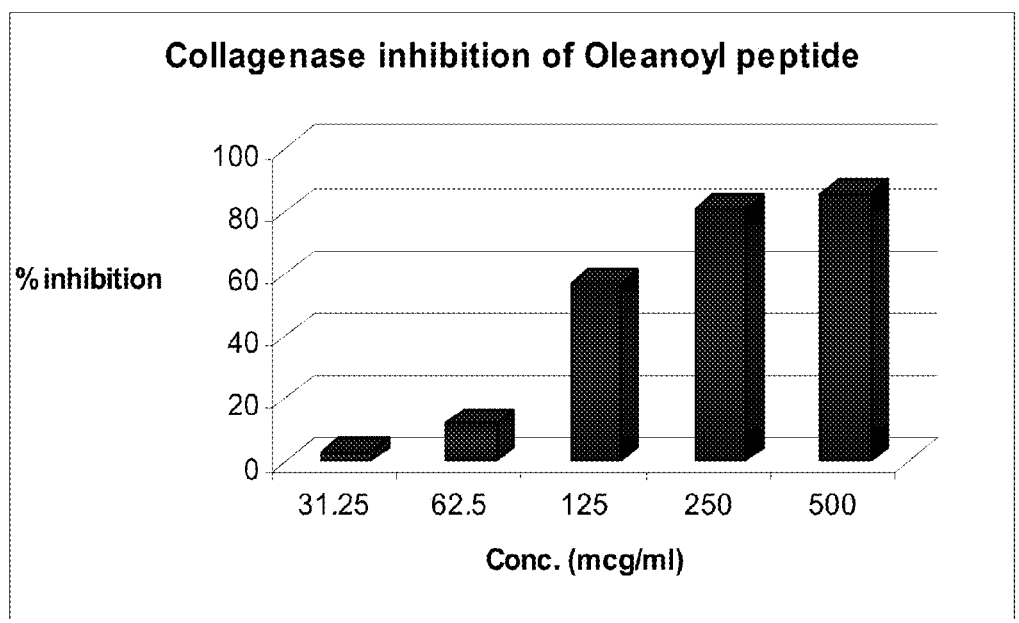

FIG. 2: provides the % inhibition of collagenase at varying concentration of Oleanoyl peptide.

Figure 3:
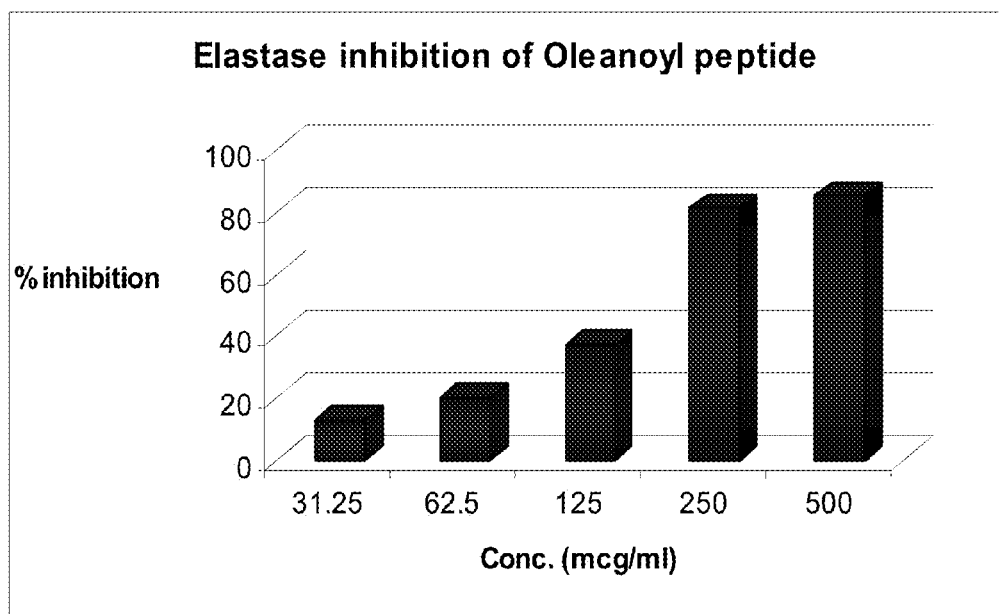

FIG. 3: provides the % inhibition of elastase at varying concentration of Oleanoyl peptide.

Figure 4:
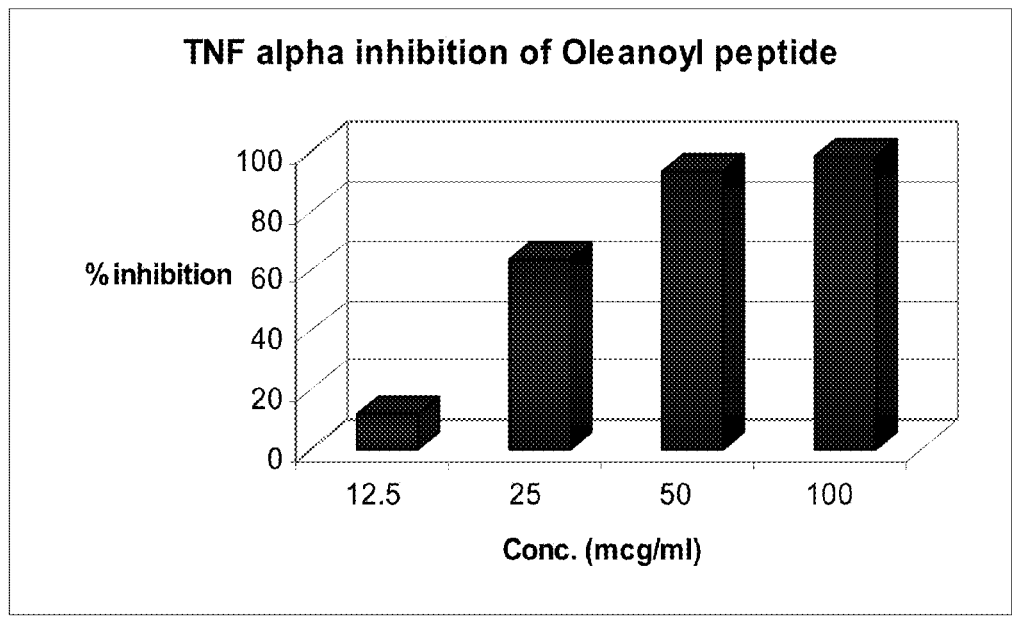

FIG. 4: represents TNF α inhibition at varying concentrations of Oleanoyl peptide.

Figure 5:
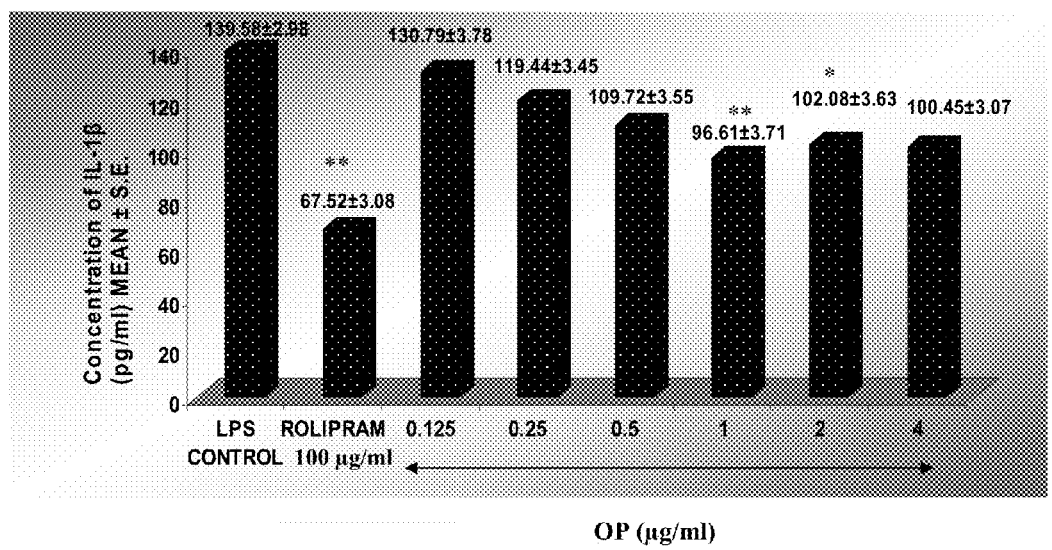

FIG. 5: Effect of Oleonoyl peptide at graded doses on expression of extracellular Interleukin-1 beta (IL-1β) from human neutrophils; P value: *<0.01; **<0.001

Figure 6:
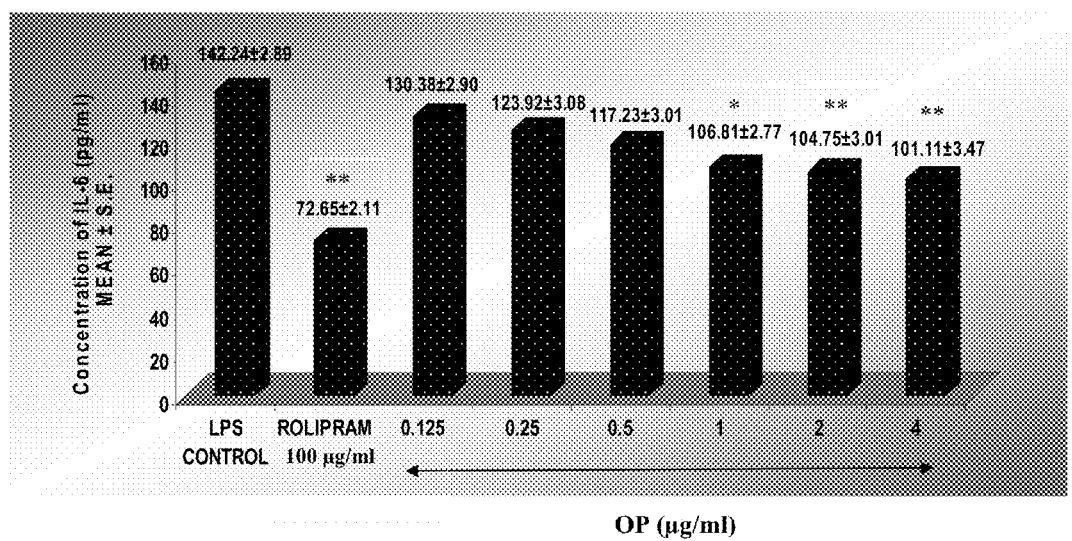

FIG. 6: Effect of Oleonoyl peptide at graded doses on expression of extracellular Interleukin-6 (IL-6) from human neutrophils; P value: *<0.01; **<0.001

Figure 7:
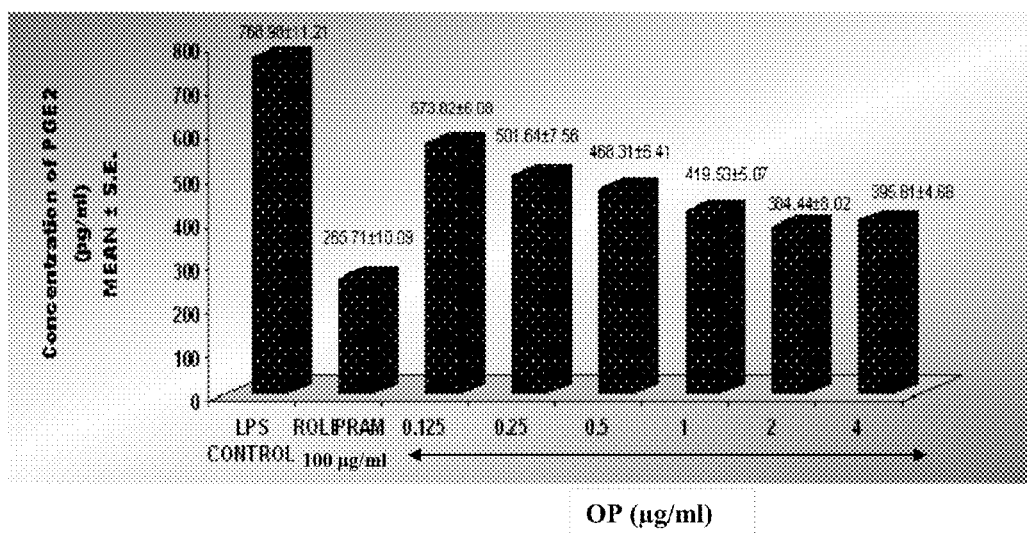

FIG. 7: Effect of Oleonoyl peptide at graded doses on expression of extracellular Prostaglandin E2 ($PGE_2$) from human neutrophils; P value: *<0.01; **<0.001

Figure 8:
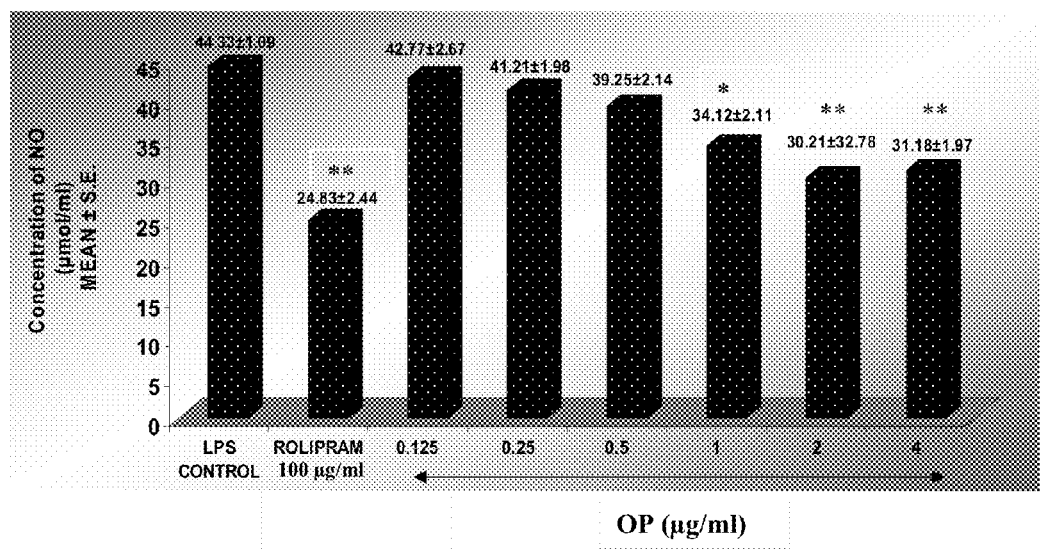

FIG. 8: Effect of Oleonoyl peptide at graded doses on expression of extracellular Nitric Oxide (NO) from human neutrophils; P value: *<0.01; **<0.001

Figure 9:
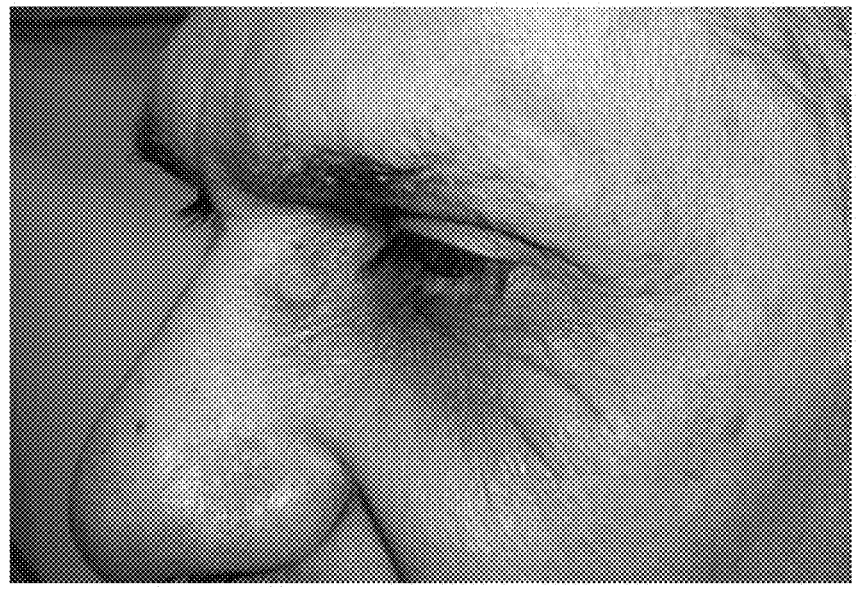
Figure 9:

FIGS. 9 (a) & 9 (b): represents a photograph of the candidate taken before and after application of Oleanoyl peptide respectively. FIG. 9 (b) shows the effect of Oleanoyl peptide in softening the wrinkles.

Figure 10:
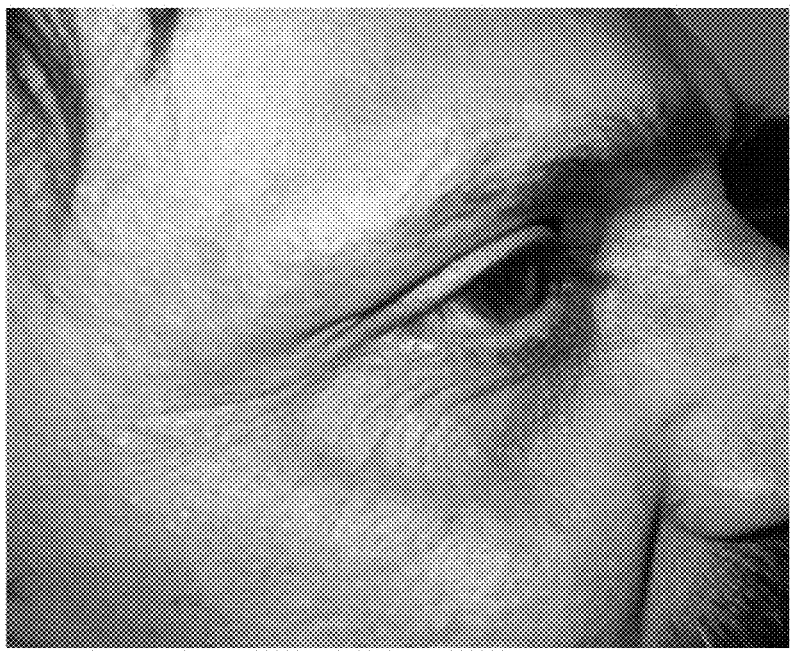
Figure 10:
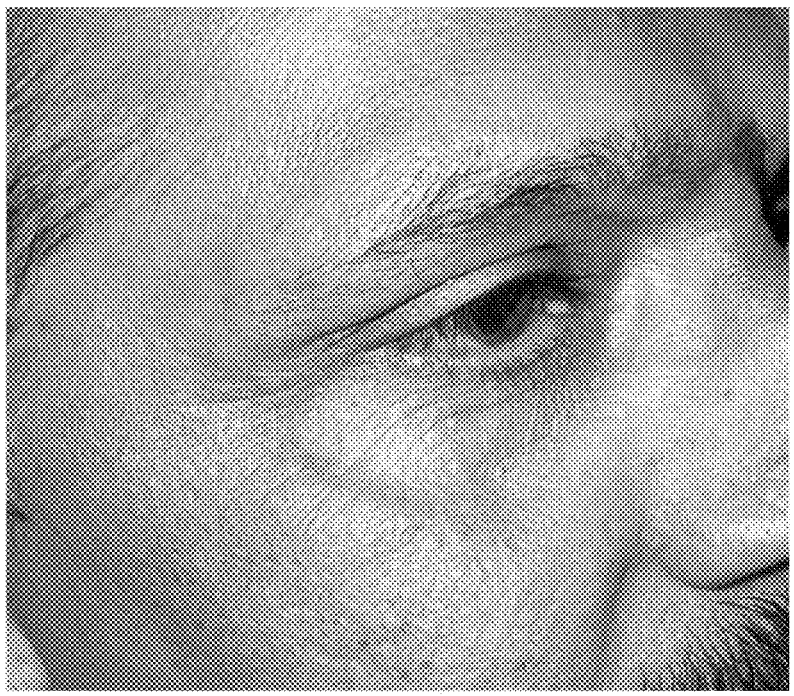

FIGS. 10 (a) & 10 (b): represents a photograph of the candidate taken before and after application of Oleanoyl peptide respectively. FIG. 10 (b) shows the effect of Oleanoyl peptide in improving the skin thickness.

Figure 11:
Figure 11:

FIGS. 11 (a) & 11 (b): represents a photograph of the candidate taken before and after application of Oleanoyl peptide respectively. FIG. 11 (b) shows the effect of Oleanoyl peptide in the reduction of hyperpigmentation.

Figure 12:
Figure 12:

FIGS. 12 (a) & 12 (b): represents a photograph of the candidate taken before and after application of Oleanoyl peptide respectively. FIG. 12 (b) shows the effect of Oleanoyl peptide in reducing dark circles under the eye.

Figure 13:
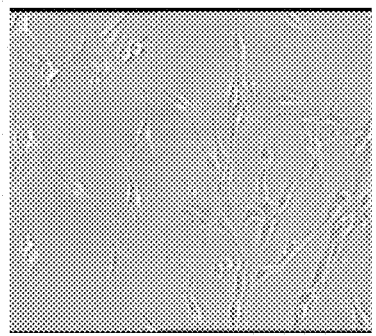
Figure 13:
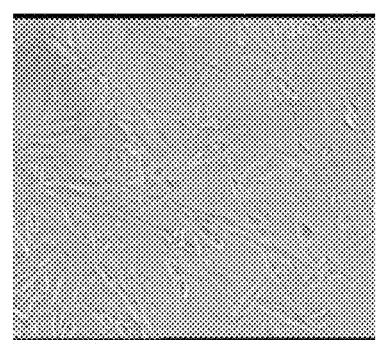
Figure 13:
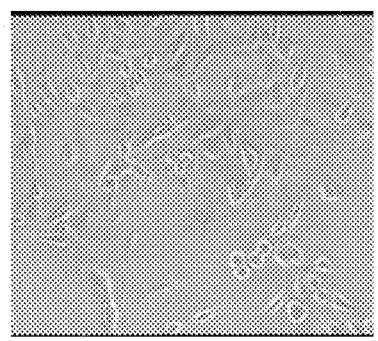
Figure 13:
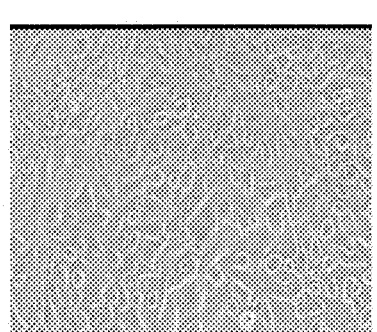

FIG. 13: Effect of the composition containing Oleanoyl peptide and coconut liquid endosperm in skin conditioning and rejuvenation; (a) Control cells without sample (b) 35% enhancement compared to untreated cells at 5 μg/ml by coconut liquid endosperm (c) 15% enhancement compared to untreated cells at 5 μg/ml by Oleanoyl peptide (d) 85% enhancement compared to untreated cells at 5 μg/ml by the composition containing Oleanoyl peptide & Coconut liquid endosperm.

Figure 14:
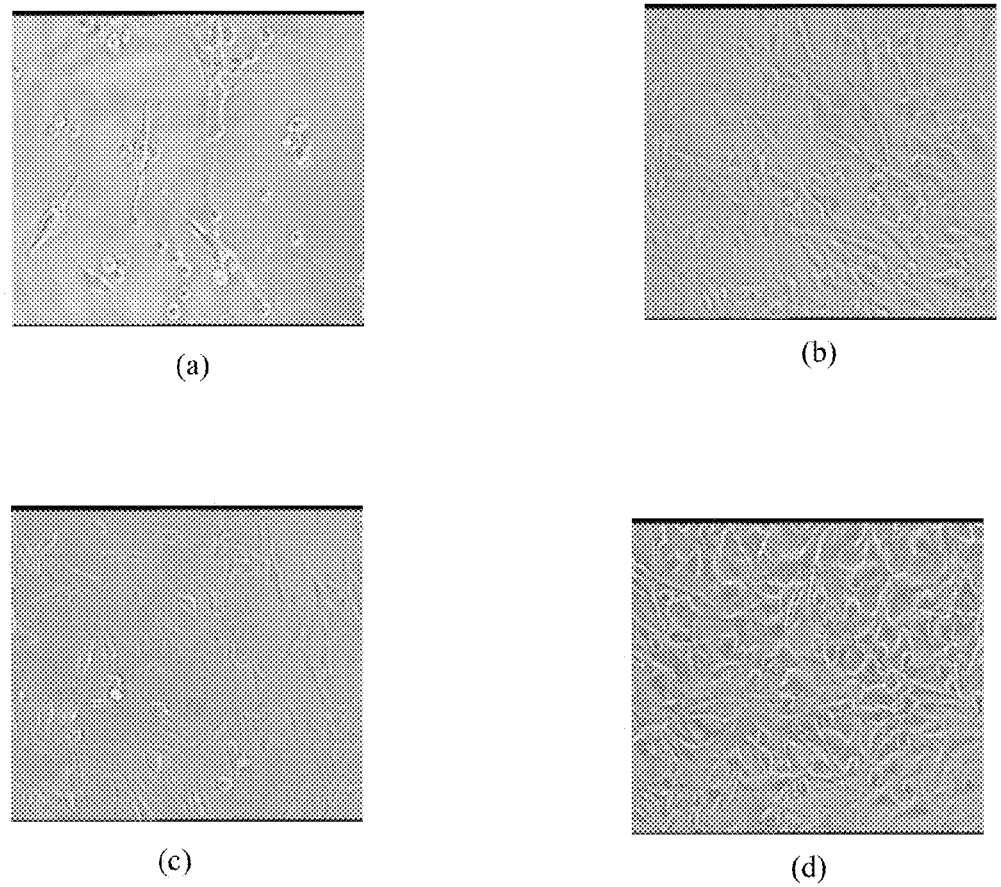

FIG. 14: Effect of the composition containing Oleanoyl peptide and amla extract in protection of skin against UV B; (a) Control cells exposed to UV without sample (b) 53% UV protection compared to untreated cells at 40 μg/ml by amla extract (c) 13% UV protection compared to untreated cells at 40 μg/ml by Oleanoyl peptide (d) 80% UV protection compared to untreated cells at 40 μg/ml by the composition containing Oleanoyl peptide & amla extract.

Figure 15:
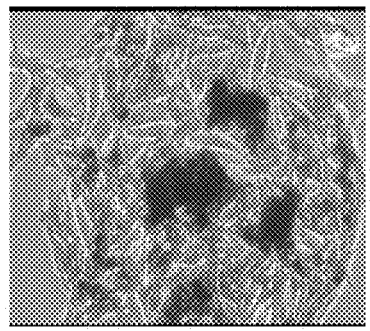
Figure 15:
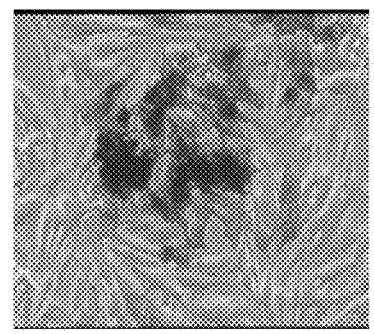
Figure 15:
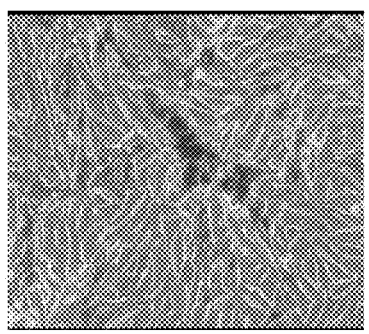
Figure 15:
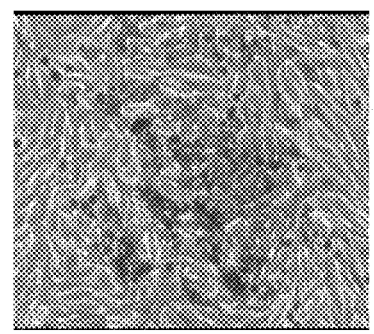
Figure 15:
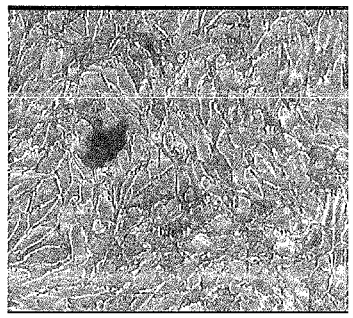
Figure 15:
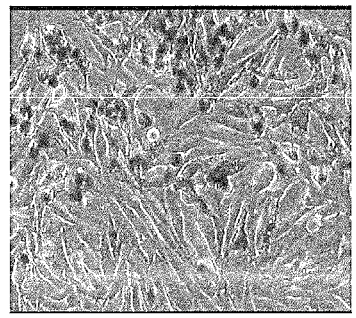
Figure 15:
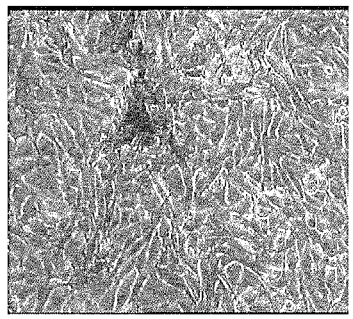
Figure 15:
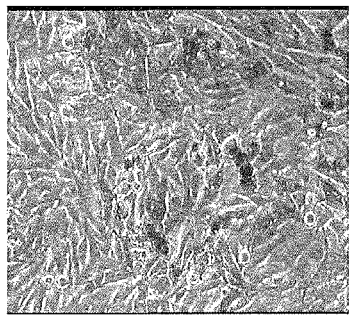

FIG. 15: Effect of the composition containing Oleanoyl peptide and stilbenes/licorice extract/THC in inhibiting melanin; (a) Control cells without sample (b) Oleanoyl peptide treatment showing no significant reduction in melanin (c) composition containing Oleanoyl peptide & pterostilbene—$IC_{50}$ is 0.34 μg/ml (d) composition containing Oleanoyl peptide & 3-hydroxypterostilbene (3HPT)—$IC_{50}$ is 0.42 μg/ml (e) composition containing Oleanoyl peptide & licorice extract—$IC_{50}$ is 1.3 μg/ml (f) composition containing Oleanoyl peptide & oxyresveratrol—$IC_{50}$ is 4.3 μg/ml (g) composition containing Oleanoyl peptide & THC—$IC_{50}$ is 1.2 μg/ml (h) composition containing Oleanoyl peptide & Resveratrol—$IC_{50}$ is 1.6 μg/ml

DETAILED DESCRIPTION OF THE INVENTION

The present invention relates to a method of treating skin aging, said method comprising step of treating the skin with a composition containing peptide of SEQ ID NO: 1 linked to oleanolic acid represented by structure I.

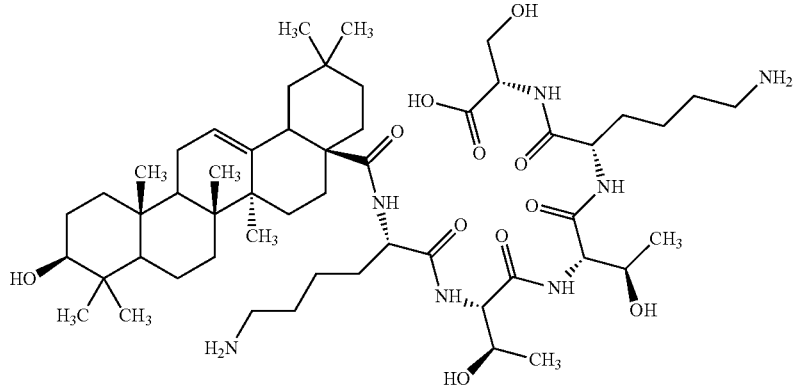

Structure I

In another embodiment of the present invention, the composition optionally comprise ingredients or plant extracts selected from a group comprising coconut liquid endosperm, amla extract, stilbenes or its derivatives, tetrahydrocurcuminoids or its derivatives, licorice extract and combinations thereof.

In still another embodiment of the present invention, the stilbenes are selected from a group comprising oxyresveratrol, pterostilbene, resveratrol, 3-hydroxypterostilbene and combinations thereof.

In still another embodiment of the present invention, the composition is applied topically and is in the form selected from a group comprising cream, lotion, gel, emulsion, patch and liquid.

The present invention relates to a composition containing peptide of SEQ ID NO: 1 linked to oleanolic acid represented by structure I and additionally one or more adjuncts selected from a group comprising sunscreen, skin-lightening agent, skin-tanning agent, antioxidant, perfume, opacifier, preservative, colorant, emulsifier, thickener and buffer formulated in a dermatologically acceptable vehicle.

DEFINITIONS

The term "topical application", as used herein, means to apply or spread the compositions of the present invention onto the surface of the skin.

Structure I

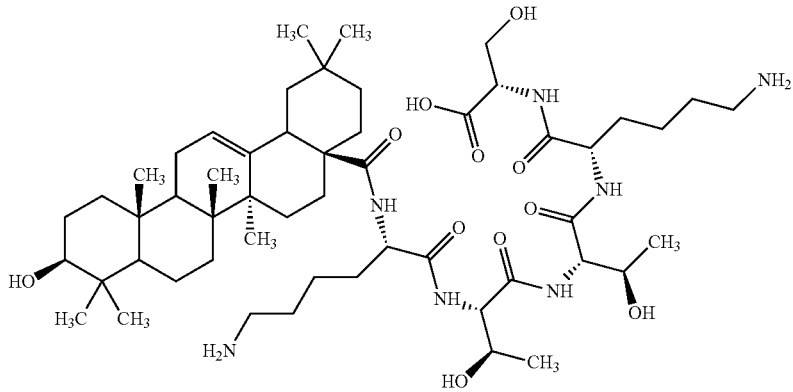

In another embodiment of the present invention, the composition optionally comprise ingredients or plant extracts selected from a group comprising coconut liquid endosperm, amla extract, stilbenes or its derivatives, tetrahydrocurcuminoids or its derivatives, licorice extract and combinations thereof.

In another embodiment of the present invention, the stilbenes are selected from a group comprising oxyresveratrol, pterostilbene, resveratrol, 3-hydroxypterostilbene and combinations thereof.

In another embodiment of the present invention, the composition is formulated for topical application and is in the form selected from a group comprising cream, lotion, gel, emulsion, patch and liquid.

The present invention relates to a peptide of SEQ ID NO: 1 linked to oleanolic acid as represented in structure I. Oleanolic acid is coupled to the terminal lysine of peptide of SEQ ID NO: 1.

The term "dermatologically-acceptable," as used herein, means that the compositions or components thereof so described are suitable for use in contact with human skin without undue toxicity, incompatibility, instability, allergic response, etc.

The term "safe and effective amount" as used herein means an amount of a compound or composition sufficient to significantly induce a positive benefit, preferably a positive skin appearance or feel benefit, including independently the benefits disclosed herein, but low enough to avoid serious side effects, i.e. to provide a reasonable benefit to risk ratio, within the scope of sound judgment of the skilled artisan.

The term "skin compatibility," as used herein means the ability of skin to tolerate long term application of topical compositions with minimal adverse skin reactions such as stinging, burning, redness, itching and folliculitis.

The term "co-administered" refers to administering the composition with a second medicinal, typically having a dif- Structure I

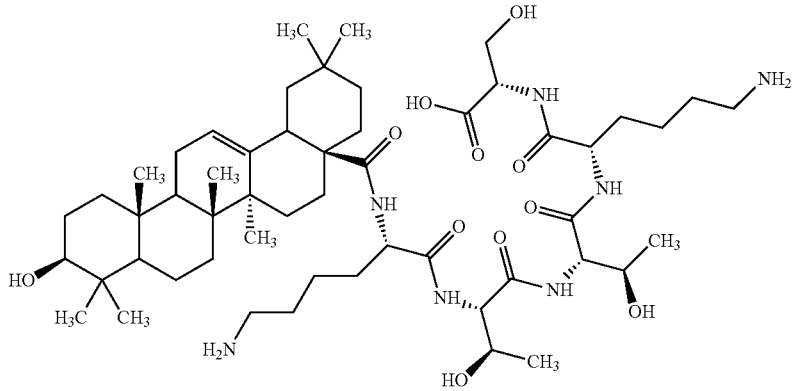

In another embodiment of the present invention, the peptide of SEQ ID NO: 1 linked to oleanolic acid is synthesized by coupling the peptide of SEQ ID NO: 1 with oleanolic acid by dehydration reaction.

fering mechanism of action, using a dosing regimen that promotes the desired result. This can refer-to simultaneous dosing, dosing at different times during a single day, or even dosing on different days. The compositions can be administered separately or can be combined into a single formulation.

The present invention provides a composition containing peptide of SEQ ID NO: 1 linked to oleanolic acid and method of treating skin aging. The peptide of SEQ ID NO: 1 linked to oleanolic acid (compound) is hereinafter referred as "Oleanoyl peptide" throughout the description.

Oleanolic acid in the compound can be replaced by its derivatives and used in the invention. Oleanolic acid part of the compound may be further modified containing substituents at 3-acyloxy groups chosen from alkanoyloxy, alkenoyloxy, arylcarboxyloyloxy, heteroarylcarboxyloyloxy groups etc Oleanoyl peptide used in the invention effectively acts by multiple mechanisms in preventing, delaying and/or reversing skin aging caused by loss of skin elasticity, collagen deformation, inflammation, free radical induced skin damage etc The composition contains Oleanoyl peptide individually or in combination with ingredients or plant extracts. The composition containing Oleanoyl peptide and ingredients or plant extracts disclosed in the invention shows synergistic effect in treating specific signs of skin aging. The ingredients or plant extracts are selected from a group comprising coconut liquid endosperm, amla extract, stilbenes or its derivatives, tetrahydrocurcuminoids or its derivatives, licorice extract and combinations thereof. Stilbenes are selected from a group comprising oxyresveratrol, pterostilbene, resveratrol, 3-hydroxypterostilbene and combinations thereof.

The concentration of Oleanoyl peptide used in the invention ranges from about 0.0001 to about 10%.

The concentration of ingredients or plant extracts used in the composition ranges from about 0.0001 to about 10%.

In one embodiment, the composition comprising Oleanoyl peptide and coconut liquid endosperm provides enhanced cell rejuvenation.

In another embodiment, the composition comprising Oleanoyl peptide and amla extract provides enhanced protection against UV induced damage.

In yet another embodiment, the composition comprising Oleanoyl peptide and stilbenes or its derivatives/licorice extract/tetrahydrocurcuminoids or its derivatives provides enhanced skin lightening.

The natural ingredients hereinafter are referred to as "active ingredients". The anti-aging skin care composition of the present invention also comprises a dermatological-acceptable vehicle. This substance may act as a diluent, dispersant or carrier for the active ingredients. The vehicle may comprise materials commonly employed in skin care products, including but not limited to water, a buffered aqueous solution, liquid or solid emollients, silicone oils, emulsifiers, solvents, humectants, thickeners, powders, propellants and the like.

The powdered components of the anti-aging skin care composition may be dissolved in suitable vehicle to increase or decrease the strength and hence the potency of the product. Such variations in strength and potency may be highly desirable in maintaining the efficacy of the anti-aging skin care composition when treating a highly heterogeneous population comprised of individuals with large variations in skin type and condition.

In addition to the active ingredients, the composition of the present invention may optionally contain various cosmetic or manufacturing adjuncts. For example, sunscreens, skin-lightening etc may also be included. The vehicle may also further include adjuncts such as antioxidants, perfumes, pacifiers, preservatives, colorants and buffers, as necessary or desirable to enhance the efficacy, storage, utility or marketability of the anti-aging skin care composition. In preferred embodiments, the addition of perfumes or other masking agents to the skin care composition is desirable and/or necessary to reduce or block the odors associated with the presence of the active ingredients.

To prepare the anti-aging skin care composition of the present invention, a variety of techniques may be employed. For example, the active ingredient(s) may be generally incorporated into the dermatologically-acceptable vehicle in the manner that is usual for the preparation of skin care products. Thus, the active ingredient(s) may first be dissolved or dispersed in a portion of the water or another solvent or liquid to be incorporated into the dermatologically-acceptable vehicle. The preferred compositions for use in this manufacturing approach are oil-in-water, water-in-oil, or water-in-oil-in-water emulsions.

However, in a preferred embodiment, the active ingredient(s), with or without the above-described adjuncts, are maintained in a separate state from the dermatologically acceptable carrier, for example as a dry powder. The resulting anti-aging skin care composition is then applied to the skin of the face, hands, arms, legs, neck or other areas where desirable by manual application to ensure complete and even coverage of the treated areas.

The anti-aging skin care composition of the present invention may be in the form of conventional "leave-on" skin-care products, including but not limited to aqueous solutions, creams, gels, lotions, sprays, ointments, pastes, mousses, cosmetics, etc. The anti-aging skin care composition can also be in the form of "wash-off" products, including but not limited to, a bath or shower gel, possibly containing a delivery system for the active ingredients to promote their adsorption or adherence to the skin during rinsing. Most preferably, the product is a "leave-on" product; a product to be applied to the skin without a deliberate rinsing step soon after its application to the skin.

The anti-aging skin care composition of the present invention may be packaged in any suitable manner, including but not limited to, a jar, a bottle, a tube, a stick, a roller-ball applicator, an aerosol spray device, etc., in the conventional manner.

The present invention further provides a method of providing skin care benefit like, delaying or preventing wrinkling; delaying or preventing sagging; delaying or preventing photo damaged skin; imparting a youthful appearance to skin; enhancing collagen deposition in skin; enhancing tissue repair and cell growth and improving skin texture, smoothness or firmness;

In preferred embodiments, the method of the present invention may be carried out one or more times daily to the skin which requires treatment. In this method, a small volume of the anti-aging skin care composition, for example from 0.1 to 5 ml, is applied to the skin from a suitable container or applicator and spread over and/or rubbed into the skin using the hands or fingers or a suitable device. A rinsing step may optionally follow depending on whether the composition is formulated as a "leave-on" or a "rinse-off" product. The improvement in skin appearance will become apparent within one or more days of use, depending on skin condition and the concentration, amount and frequency with which the anti-aging skin care composition is used.

The inventive compositions, methods and uses described herein result in the prevention, reduction or delay in the formation of wrinkles and prevention, reduction or delay in loss of skin tone. The compositions, methods and uses described herein also improve dark spots, skin texture, smoothness or firmness, and create smooth and supple skin with improved elasticity. A general improvement in the appearance, texture and condition, in particular with respect to the radiance, clarity, and general youthful appearance of skin is achieved. The present invention therefore provides a wide range of results that are collectively described as anti-aging benefits provided by Oleanoyl peptide.

The inventive compositions, methods and uses described herein are further useful for topical application and for regulating skin condition, including visible and/or tactile discontinuities in skin (especially the skin surface; such discontinuities are generally undesirable). Such discontinuities may be induced or caused by internal and/or external factors, and include the signs of skin aging described herein.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g. chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g. associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, redness or discoloration (including under eye circles), blotching, sallowness, hyper pigmented skin regions such as age spots and freckles, keratoses, abnormal differentiation, hyperkeratinization, elastosis, collagen breakdown, and other histological changes in the stratum corneum, dermis, epidermis, the skin vascular system (e.g. telangiectasia or spider vessels) and underlying tissues, especially those proximate to the skin.

It is to be understood that the present invention is not to be limited to prevention, reduction or delay of the above mentioned "signs of skin aging" which arise due to mechanisms associated with skin aging, but is intended to include prevention, reduction or delay of said signs irrespective of the mechanism of origin.

EXAMPLES

The above features and other advantages of the present invention will be more clearly understood from the following detailed description taken in conjunction with the examples.

*Olea europaea* extract: It is a cream colored powder with active component triterpenoid Oleanolic acid, more than 90% pure. Source is *Olea europaea* (olive) leaves.

Pentapeptide, Lysyl-Threonyl-Threonyl-Lysyl-Serine (SEQ ID NO: 1): It is a peptide of the general sequence Lysyl-Threonyl-Threonyl-Lysyl-Serine that is a product of collagen degradation (K. Katayama, J. A. Borunda, R. Raghow, A. H. Kang, J. M. Sayer, J. Biol. Chem., 268, 9941 (1993).

Example 1

Pentapeptide of SEQ ID No. 1 linked to the triterpenoid Oleanolic acid (oleanolic acid is attached to the terminal lysine of peptide of SEQ ID NO: 1), synergistically reduces or delays the symptoms of ageing by maintaining a healthy balance in the collagen synthesis and collagen breakdown in the dermal matrix of skin.

Thus, the Oleanoyl peptide is endowed with all the anti ageing modes of action such as the Serine protease inhibitory activity, anti-inflammatory activity, antioxidant activity, collagen boosting activity etc.

The topical cosmetic compositions of the present invention containing the Oleanoyl peptide individually or in combination with ingredients or plant extracts is prepared in liquid or semi solid form by mixing with base ingredients, adjuvants and additives commonly used in the cosmetics field. Cosmetics in liquid or semi solid form include but are not limited to the skin lotions, creams and gels.

The compositions for topical application can also be used in body lotions, peel off and face mask cosmetic formulations.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Example 1

Chemical Synthesis of Oleanoyl Peptide

Acetyloleanoyl Lys (Z)-Thr (Bzl)-Thr (Bzl)-Lys (Z)-Ser (Bzl)-OBzl

Acetyloleanolic acid (5 GMs, 10 mmoles) is dissolved in 50 ml of chloroform and cooled to 0° C. 20 ml of freshly distilled thionyl chloride is added drop wise to the reaction mixture. The mixture was stirred at low temperature for 30 min and then at room temperature for 2 h. Solvents are then completely removed in vacuo and the residue is dried. TFA.Lys (Z)-Thr (Bzl)-Thr (Bzl)-Lys (Z)-Ser (Bzl)-OBzl (9.3 GMs, 7.14 mmoles) is taken with 100 ml of chloroform and cooled to 0° C. Under stirring, 5 ml of triethylamine is added and pH of this solution is adjusted to 8-9. The pentapeptide solution is cooled to 10° C. and under stirring acetyloleanoyl chloride solution prepared above (in 25 ml of chloroform) is slowly added. The mixture is stirred at low temperature for 15 min and at room temperature till completion of reaction. The reaction mixture is then washed with 10% $KHSO_4$ solution (3 times), water, saturated $NaHCO_3$ solution (3 times), water and saturated NaCl solution. It is finally dried over anhydrous $Na_2SO_4$ and concentrated in vacuo. The residue is precipitated using ethyl acetate/petroleum ether (7:3). The precipitate is then filtered and dried in vacuo. Yield 114 g (80%). The mass spectrum indicated the desired m/e peak at 1673 and high resolution NMR was conforming to desired structure.

Acetyloleanoyl-Lys-Thr-Thr-Lys-Ser-OH
(acetyloleanolic acid attached to SEQ ID NO: 1)

Acetyloleanoyl-Lys (Z)-Thr (Bzl)-Thr (Bzl)-Lys (Z)-Ser (Bzl)-OBzl (10 GMs, 6 mmoles) is mixed with 100 ml of 5% acetic acid in methanol and transferred to a hydrogenator. 2 g of 10% Pd—C is added to the reaction mixture. Hydrogenation is carried out at a temperature of 60° C. using hydrogen pressure of 5 kg. After completion of reaction, catalyst was filtered off and the reaction mixture was concentrated in vacuo. The residue was precipitated by adding Acetonitrile. The solid was filtered and dried. Yield 5.6 g (90%). Mass spectrum showed molecular ion peak at 1045

Oleanoyl-Lys-Thr-Thr-Lys-Ser-OH (Oleanoyl peptide-Oleanolic acid attached to SEQ ID NO: 1)

Acetyloleanoyl-Lys-Thr-Thr-Lys-Ser-OH (acetyloleanolic acid attached to SEQ ID NO: 1) obtained above (5 GMs, 4.8 mmoles) was taken up in 25 ml of methanol and stirred. To this mixture, 25 ml of 2M LiOH solution was added and stirred for 2 hours. Methanol was stripped from the reaction mixture. The aqueous solution washed with ethyl acetate and acidified with 1N HCl solution to pH 7-8. The aqueous solution was then evaporated to dryness. To the residue, methanol was added and insoluble salts was filtered off. The solution was concentrated and precipitated using dry diethyl ether. The solid (Oleanoyl peptide) was then filtered and dried. Yield 4.1 g (85%). ES-MS spectrum showed molecular ion peak at m/e1001 (M-H).

The attachment of oleanolic acid to the pentapeptide of SEQ ID NO: 1 (Lysyl-Threonyl-Threonyl-Lysyl-Serine) (FIG. 1) significantly enhances the anti-aging potential of the pentapeptide with multiple modes of action. Thus, oleanoyl peptide of the invention serves as a better and novel molecule for treating skin conditions.

Example 2

Anti Ageing Potential of Oleanoyl Peptide

In-Vitro Study:
Collagenase Inhibitory Potential:

Collagenase inhibitory potential of Oleanoyl peptide was determined by using Molecular Probes EnzChek® Collagenase Assay Kit that provides high sensitivity required for screening inhibitors in a high-throughput format. The EnzChek kit contains DQgelatin, fluorescein conjugated gelatin. This substrate is efficiently digested by most of the gelatinases and collagenases to yield highly fluorescent peptides. The increase in fluorescence is proportional to proteolytic activity and can be monitored with a fluorescence microplate reader. The reduction in fluourescence is directly proportional to the collagenase inhibitory activity of the sample. Collagenase used for the assay is purified from *Clostridium histolyticum*. Using 100 μg/mL DQ gelatin and a 30 minute incubation period, the assay can detect the activity of this enzyme down to a final concentration of $2\times10^{-3}$ U/mL (7 ng protein/mL), where one unit is defined as the amount of enzyme required to liberate 1 μmole of L-leucine equivalents from collagen in 5 hours at 37° C., pH 7.5.

Varying concentrations of Oleanoyl peptide in suitable vehicle (PBS or 2% DMSO that does not affect the fluorescence intensity) were pre-incubated for 10 minutes with 12.5 μg/ml substrate, DQ gelatin (from pig skin), fluorescein conjugate and then 0.2 U/ml of Collagenase Type IV from *Clostridium histolyticum* enzyme was added. The fluorescence intensity was measured after 30 minutes (Em: 485 nm and Ex: 520 nm.) in microplate reader. The dose dependent inhibitory activity of Oleanoyl peptide is calculated and the results are expressed as $IC_{50}$ values using Graphpad prism software. The percentage of inhibition of collagenase is calculated as follows, % Inhibition=$[(C-T)/C]\times100$ Where C=absorbance due to collagenase activity in the absence of inhibitor
T=absorbance due to collagenase activity in the presence of inhibitor
$IC_{50}$ value is the concentration required for 50% inhibition of the collagenase activity and hence, lower $IC_{50}$ value indicates better collagenase inhibitory potential. From table 1, it is evident that Oleanoyl peptide shows significant collagenase inhibitory activity when compared to Oleanolic acid, peptide of SEQ ID NO: 1 and Pal-Lys-Thr-Thr-Lys-Ser (Palmitoyl group attached to SEQ ID NO: 1) individually.

FIG. 2 provides the % inhibition of collagenase at varying concentration of Oleanoyl peptide.

Elastase Inhibitory Potential:

Elastase inhibitory potential of Oleanoyl peptide was determined by using Molecular Probes EnzChek® Elastase Assay Kit that provides high sensitivity required for screening inhibitors in a high-throughput format. The EnzChek kit contains DQelastin, fluorescein conjugated soluble bovine neck ligament elastin. This substrate is efficiently digested by elastase to yield highly fluorescent peptides. The increase in fluorescence is proportional to proteolytic activity and can be monitored with a fluorescence microplate reader. The reduction in fluourescence is directly proportional to the elastase inhibitory activity of the sample. Elastase used for the assay is purified from porcine pancreas.

Varying concentrations of Oleanoyl peptide in suitable vehicle (PBS or 2% DMSO that does not affect the fluorescence intensity) were pre-incubated for 10 minutes with the substrate, 25 μg/ml of DQ Elastin (from bovine neck ligament) fluorescein conjugate and 0.1 U/ml porcine pancreatic elastase enzyme was added. The fluorescence intensity was measured after 30 minutes (Em: 485 nm and Ex: 520 nm) in microplate reader. The dose dependent inhibitory activity of samples is calculated and the results are expressed as $IC_{50}$ values using Graphpad prism software. The percentage of inhibition of elastase is calculated as follows, % Inhibition=$[(C-T)/C]\times100$ Where C=absorbance due to elastase activity in the absence of inhibitor
T=absorbance due to elastase activity in the presence of inhibitor
$IC_{50}$ value is the concentration required for 50% inhibition of the elastase activity and hence, lower $IC_{50}$ value indicates better elastase inhibitory potential. $IC_{50}$ value of Oleanoyl peptide (table 1) is clearly indicative that it shows better elastase inhibitory potential than Pal-Lys-Thr-Thr-Lys-Ser (Palmitoyl group attached to SEQ ID NO: 1). Oleanolic acid and peptide of SEQ ID NO: 1 did not show elastase inhibition individually.

FIG. 3 provides the % inhibition of elastase at varying concentration of Oleanoyl peptide.

Collagen Enhancement:

Collagen enhancement facilitates the repair of skin damage due to various stress conditions.

Collagen enhancement was determined by using Sirius Red stain that binds with a greater specificity to Collagen type I and Collagen type III of the extracellular matrix. The stain bound to the collagen is dissolved and the optical density (OD) is measured spectrophotometrically using a Fluostar optima microtiter plate reader at 544 nm. The OD of the stain bound to collagen is directly proportional to the collagen content in the cells.

Human osteosarcoma cells from human bone were used for collagen enhancement studies. The cells were seeded with a seeding density of 10000 cells per well of a 24 well plate. Confluent monolayers of cells were initially treated with varying non cytotoxic concentrations of Oleanoyl peptide and vehicle (control) in the culture medium. For each concentration, 4 replicates were maintained and the analysis was performed twice such that the 'n' value is 8. After sample treatment, the cells were incubated in a $CO_2$ incubator for 48 hrs.

The cells were then developed by Sirius red staining technique to analyze the collagen enhancement. The cells were washed extensively with PBS. The cells were fixed using Bouin's fluid containing 1.3% picric acid, 35% formaldehyde and glacial acetic acid in 15:5:1 ration by incubating with 1 ml of Bouin's fluid per well for 1 hr at RT. The fixative is then removed by suction with micropipette and the cells were washed under running tap water for 15 minutes. After air drying the culture plate, the cells were stained using 0.1% Sirius red stain in 1.3% picric acid. 1 ml per well Sirius red stain was added and the cells were incubated for 1 hr under mild shaking of 70 RPM at RT in Orbitek Shaker. The stain was then removed by suction and the cells were extensively washed with 0.01N HCl to remove unbound dye. The dye bound to collagen was then dissolved in 0.2 ml of 0.1N NaOH per well for 30 minutes under mild shaking of 70 RPM in Orbitek Shaker at RT. The dye was then transferred to 96 well microplate and the OD was read at 544 nm in Fluostar Optima microplate reader.

The percentage enhancement in collagen with respect to the untreated cells considering the OD of untreated cells as optimal under normal conditions is calculated as follows, % enhancement in cell growth=$[(100/C) \times T]-100$ Where C=absorbance due to collagen in untreated cells
T=absorbance due to collagen in sample treated cells It was observed that Oleanoyl peptide showed 17% enhancement in collagen at 1.25 ppm, Pal-Lys-Thr-Thr-Lys-Ser (Palmitoyl group attached to SEQ ID NO: 1) showed 11% enhancement in collagen at 1.25 ppm, peptide of SEQ ID NO: 1 showed 5% enhancement in collagen at 1.25 ppm, while Oleanolic acid did not show any enhancement. It is clear that Oleanoyl petide shows better collagen enhancement in comparison to others.

Antioxidant Potential:
DPPH (1,1-Diphenyl-2-picrylhydrazyl radical) Scavenging Assay:

The DPPH assay is often used to evaluate the ability of antioxidants to scavenge free radicals which are known to be a major factor in biological damages caused by oxidative stress. This assay is known to give reliable information concerning the antioxidant ability of the tested compounds. The assay is based on the color change of the stable free radical DPPH from purple to yellow as the radical is quenched by the antioxidant.

The assay mixture tubes containing 1.5 ml of 0.1 mM DPPH methanolic solution and varying concentrations of the sample in a total volume of 3 ml were incubated at 37° C. for 30 minutes in a shaking water bath. The reduction in absorbance which is directly proportional to the radical scavenging is measured spectrophotometrically at 517 nm. The dose dependent free radical scavenging activity of samples is calculated and the results are expressed as $SC_{50}$ values using Graphpad prism software. The percentage of scavenging is calculated as follows, % scavenging=$[(C-T)/C] \times 100$ Where C=absorbance in the absence of inhibitor
T=absorbance in the presence of inhibitor $SC_{50}$ value is the concentration required for 50% scavenging of free radicals and hence, lower $SC_{50}$ value indicates better antioxidant potential. It is apparent from table 1 that only Oleanoyl peptide shows DPPH scavenging activity.

Anti Inflammatory Potential:
TNF α Inhibitory Potential:

For TNF α inhibitory study, human whole blood is used. In whole blood assay, monocytes appear to be the main source of TNF-α on lipopolysaccharide (LPS) stimulation. Monocyte and macrophages are a major source of TNF-α in addition to other cell types like eosinophils, mast cells, peripheral lymphocytes and granulocytes. The activation of inflammatory cells is influenced by the intracellular levels of c-AMP which are regulated by the phosphodiesterase isoenzyme. LPS is the most potent stimulus of TNF-α production in human blood. After stimulation, the assay employs the quantitative sandwich enzyme immunoassay technique. A monoclonal antibody specific for TNF-α has been pre-coated onto a microplate. TNF-α present in the sample is bound by the immobilized antibody. After washing away any unbound substances, an enzyme-linked polyclonal antibody specific for TNF-α is added. Following a wash to remove any unbound antibody-enzyme reagent, a substrate solution is added to the wells and colour develops in proportion to the amount of TNF-α bound in the initial step. The colour development is stopped and the intensity of the colour is directly proportional to the TNF-α content.

Heparinized blood from healthy donors was diluted 1:3 in RPMI 1640 culture medium containing 10% FBS. Diluted blood samples were pre-incubated with varying concentrations of Oleanoyl peptide in suitable vehicle (PBS or 0.1% DMSO) for 1 hr at 37° C. in an incubator with 5% $CO_2$. 0.1% DMSO was used as vehicle for water insoluble samples. After pre-incubation, the whole blood cells were stimulated by 1 ng/mL LPS for the release of TNF α from the macrophages by incubating for 5 hr at 37° C. in an incubator with 5% $CO_P$. The samples were then centrifuged at 3000 g for 3 minutes at 4° C. and the supernatant was assayed for TNF α content by using the TNF α Elisa kit. 200 μL of supernatant from all the tubes was transferred into microtiter plate in respective wells (Pre-coated mouse monoclonal antibody microplate) followed by the addition of 50 μL of assay diluents in all the wells. After incubation for 2 hr at room temperature, the wells were washed thoroughly with wash buffer provided and then 200 μL of conjugate was added to each well. The plate was incubated for 2 hr at room temperature. After washing again, 200 μL of substrate solution was added to each well and incubated for 20 minutes at room temperature. 50 μL of Stop Solution to each well which will cause the colour change in the wells from blue to yellow was added. The optical density was read at 450 nm which is directly proportional to TNF α content and the percentage of inhibition of TNF α content on treatment with sample was calculated with respect to that of the untreated cells. The dose dependent inhibitory activity of samples was calculated and the results were expressed as $IC_{50}$ values using Graphpad prism software. The percentage of inhibition of elastase is calculated as follows, % Inhibition=$[(C-T)/C] \times 100$ Where C=absorbance due to TNF α in the absence of inhibitor
T=absorbance due to TNF α in the presence of inhibitor $IC_{50}$ value is the concentration required for 50% inhibition of TNF α and hence, lower $IC_{50}$ value indicates better TNF α inhibitory potential.

The above procedure is also followed for determining LTB4 inhibition by Oleanoyl peptide. From the results tabulated in table 1, it is clear that Oleanoyl peptide is a better TNF α and LTB4 inhibitor.

FIG. 4 represents TNF α inhibition at varying concentrations of Oleanoyl peptide.

TABLE 1

Invitro-study on the anti-aging potential of Oleanoyl peptide

| Compound | Elastase inhibition (IC50 µg/ml) | Collagenase inhibition (IC50 µg/ml) | TNF α inhibition (IC50 µg/ml) | LTB4 inhibition | Anti-oxidant activity by DPPH Method |
|---|---|---|---|---|---|
| Oleanoyl peptide | 143 | 119 | 21 | 26% inhibition at 0.625 µg/ml | 29% inhibition at 300 µg/ml |
| Oleanolic acid | Nil | 129 | 17% inhibition at 100 µg/ml | Nil | Nil |
| Peptide of SEQ ID No. 1 | Nil | 24% inhibition at 500 µg/ml | Nil | Nil | Nil |
| Pal-Lys-Thr-Thr-Lys-Ser (Palmitoyl group attached to SEQ ID No. 1) | 16% inhibition at 500 µg/ml | 38% inhibition at 500 µg/ml | Nil | Nil | Nil |

Oleanoyl peptide also showed inhibition for IL-1β expression. The revealed maximum inhibition was of 31.78% inhibition of IL-1β expression at 1 µg/ml concentrations (Table-2, FIG. 5).

Experimental observations were made in human neutrophil that were challenged with LPS. Cell culture supernatant measurements revealed a significant reduction in the expression of IL-6 of 28.03% at 4 µg/ml (Table-3, FIG. 6). Rolipram at 100 µg/ml dose level was used as a standard drug to observe the authenticity and reproducibility of the experimental design.

The Oleanoyl peptide was also screened for NO and $PGE_2$ expression. They revealed maximum of 31.85% and 50.00% inhibition of NO and $PGE_2$ expression at 2 µg/ml concentration (Table-4, FIG. 7; Table 5, FIG. 8).

The ability of oleanoyl peptide to inhibit inflammatory markers like TNF α, IL-1β, IL-6, LTB4, NO and $PGE_2$ is indicative of its role in treating skin aging due to inflammation.

TABLE 2

Effect of Oleanoyl peptide (OP) at graded doses on expression of extracellular Interleukin-1beta(IL-1β) from human neutrophils

| Sl No. | Samples | Concentration of Test sample (µg/ml) | Concentration of IL-1β produced (pg/ml) Mean ± S.E. | % activity IL-1β expression against LPS control |
|---|---|---|---|---|
|  | LPS control | — | 139.58 ± 2.98 | — |
| 1 | OP | 0.125 | 130.79 ± 3.07 | 6.29↓ |
| 2 | OP | 0.25 | 119.44 ± 2.23 | 14.42↓ |
| 3 | OP | 0.5 | 109.72 ± 3.21 | 21.39↓ |
| 4 | OP | 1 | 96.61 ± 3.63** | 30.78↓ |
| 5 | OP | 2 | 102.08 ± 2.61* | 26.86↓ |
| 6 | OP | 4 | 100.45 ± 3.78* | 28.03↓ |
|  | Rolipram (Standard) | 100 | 67.52 ± 2.07** | 51.62↓ |

No. of Observations-3; LPS Control: Lipopolysaccharide Control;

↓: inhibition of IL-1β expression;

P value:

*<0.01;

**<0.001

TABLE 3

Effect of Oleanoyl peptide (OP) at graded doses on expression of extracellular Interleukin-6 (IL-6) from human neutrophils

| S. no. | Samples | Concentration of Test sample (µg/ml) | Concentration of IL-6 produced (pg/ml) Mean ± S.E. | % activity IL-6 expression against LPS control |
|---|---|---|---|---|
|  | LPS control | — | 142.24 ± 1.87 | — |
| 1 | OP | 0.125 | 130.38 ± 2.11 | 8.33↓ |
| 2 | OP | 0.25 | 123.92 ± 2.09 | 12.87↓ |
| 3 | OP | 0.5 | 117.23 ± 2.84 | 17.58↓ |
| 4 | OP | 1 | 106.81 ± 3.79* | 24.90↓ |
| 5 | OP | 2 | 104.75 ± 5.31** | 26.35↓ |
| 6 | OP | 4 | 101.11 ± 2.87** | 28.91↓ |
|  | Rolipram (Standard) | 100 | 72.65 ± 2.07** | 48.92↓ |

No. of Observations-3; LPS Control: Lipopolysaccharide Control;
↓: inhibition of IL-6 expression;
P value:
*<0.01;
**<0.001

TABLE 4

Effect of Oleanoyl peptide (OP) at graded doses on expression of extracellular Prostaglandin E2 ($PGE_2$) from human neutrophils

| S. no. | Samples | Concentration of Test sample (µg/ml) | Concentration of $PGE_2$ produced (pg/ml) Mean ± S.E. | % activity $PGE_2$ expression against LPS control |
|---|---|---|---|---|
|  | LPS control | — | 768.98 ± 11.21 | — |
| 1 | OP | 0.125 | 573.82 ± 6.08 | 25.37↓ |
| 2 | OP | 0.25 | 501.64 ± 7.56 | 34.76↓ |
| 3 | OP | 0.5 | 468.31 ± 6.41* | 39.09↓ |
| 4 | OP | 1 | 419.53 ± 5.07** | 45.44↓ |
| 5 | OP | 2 | 384.44 ± 8.02** | 50.00↓ |
| 6 | OP | 4 | 395.81 ± 4.68** | 48.52↓ |
|  | Rolipram (Standard) | 100 | 265.71 ± 10.09** | 65.44↓ |

No. of Observations-3; LPS Control: Lipopolysaccharide Control;
↓: inhibition of NO expression;
P value:
*<0.01;
**<0.001

TABLE 5

Effect of Oleanoyl peptide (OP) at graded doses on expression of extracellular Nitric Oxide (NO) from human neutrophils

| S. no. | Samples | Concentration of Test sample (µg/ml) | Concentration of NO produced (µmol/ml) Mean ± S.E. | % activity NO expression against LPS control |
|---|---|---|---|---|
|  | LPS control | — | 44.33 ± 1.01 | — |
| 1 | OP | 0.125 | 42.77 ± 1.42 | 3.51↓ |
| 2 | OP | 0.25 | 41.21 ± 1.05 | 7.03↓ |
| 3 | OP | 0.5 | 39.25 ± 1.08 | 11.45↓ |
| 4 | OP | 1 | 34.12 ± 2.00* | 23.03↓ |
| 5 | OP | 2 | 30.21 ± 1.18** | 31.85↓ |
| 6 | OP | 4 | 31.18 ± 1.20** | 29.66↓ |
|  | Rolipram (Standard) | 100 | 24.83 ± 2.07** | 43.98↓ |

No. of Observations-3; LPS Control: Lipopolysaccharide Control;
↓: inhibition of NO expression;
P value:
*<0.01;
**<0.001

Example 3

Study on the Effect of Oleonoyl Peptide on Humans

To study the potential effect of Oleanoyl peptide on human skin, candidates were selected in-house whose age ranging from about 30 to 60 with moderate to severe signs of aging. A topical composition comprising Oleanoyl peptide (0.01%) was prepared as a cream for application on the skin.

The cream containing Oleanoyl peptide was applied on the affected areas of facial skin of the candidates twice daily for a continuous period of three weeks. Photographs of the candidates were taken before and after three weeks of application of the cream.

FIGS. 9 (a) and 9 (b) represents a photograph of the candidate taken before and after application of Oleanoyl peptide. It is evident that the wrinkles are softened after application of oleanoyl peptide.

FIGS. 10 (a) and 10 (b) represents a photograph of the candidate taken before and after application of Oleanoyl peptide. It is evident that there is an improvement in skin thickness after application of oleanoyl peptide.

FIGS. 11 (a) and 11 (b) represents a photograph of the candidate taken before and after application of Oleanoyl peptide. It is evident that there is a reduction in hyperpigmentation after application of oleanoyl peptide.

FIGS. 12 (a) and 12 (b) represents a photograph of the candidate taken before and after application of Oleanoyl peptide. It is evident that there is a reduction of dark circles under the eye after application of oleanoyl peptide.

All these evidences are clearly indicative of the multifunctional anti aging potential of Oleanoyl peptide.

Example 4

Preparation of Compositions Containing Oleanoyl Peptide and Ingredients or Plant Extracts In one embodiment of the present invention, various ingredients and plant extracts are used in combination with Oleanoyl peptide. Specific components are selected from the group comprising coconut liquid endosperm, amla extract, stilbenes or its derivatives, licorice extract and tetrahydrocurcuminoids or its derivatives. These components are either used individually with Oleanoyl peptide or in combinations. The dry powder of the component(s) and that of the Oleanoyl peptide is mixed in determined ratios, dissolved in water or any other solvent to arrive at the composition. Each component used in the invention with Oleanoyl peptide shows significant activity for treating specific signs of skin aging.

Composition Containing Oleanoyl Peptide and Coconut Liquid Endosperm for Enhanced Skin Rejuvenation Cell Proliferation Enhancement:

Swiss 3T3 mouse fibroblast cells were used for cell proliferation studies. The cells were seeded with a seeding density of 3000 cells per well of a 96 well plate in DMEM medium. Confluent monolayers of Swiss 3T3 fibroblast cells were treated with varying non cytotoxic concentrations of sample (composition containing Oleanoyl peptide and coconut liquid endosperm) and vehicle (control) in the culture medium without FBS. For each concentration, 6 replicates were maintained and the analysis was performed twice such that the 'n' value is 12. After sample treatment, the cells were incubated in a $CO_2$ incubator for 72 hrs. The cells were then developed by NRU staining technique to analyze the cell viability. The cells were incubated with 0.003% solution of neutral red prepared in pre warmed DMEM medium for 3 hrs at 37° C. in $CO_2$ incubator. The excess dye was then washed off with phosphate buffer saline (PBS). The lysosomal dye was extracted in 100 µl of developer solution consisting of 25 ml of water, 24.5 ml of ethanol and 0.5 ml of glacial acetic acid at RT for 20 min. The optical density (OD) was read at 492 nm using a Fluostar optima microplate reader.

The percentage enhancement in cell growth with respect to the untreated cells considering the OD of untreated cells as optimal under normal conditions is calculated as follows, $$\% \text{ enhancement in cell growth} = [(100/C) \times T] - 100$$

Where C=absorbance due to cell growth in untreated cells
T=absorbance due to cell growth in sample treated cells The results tabulated in table 6 and FIG. 13 shows that the cell proliferation is significantly enhanced in cells treated with the composition containing Oleanoyl peptide and coconut liquid endosperm, thus indicating the composition is useful for skin rejuvenation.

TABLE 6

| Product | Cell proliferation enhancement |
| --- | --- |
| Coconut liquid endosperm | 35 ± 5% enhancement compared to untreated cells at 5 µg/ml conc. |
| Oleanoyl peptide | 15 ± 2% enhancement compared to untreated cells at 5 µg/ml conc. |
| Composition of Coconut liquid endosperm & Oleanoyl peptide (1:1) | 85 ± 8% enhancement compared to untreated cells at 5 µg/ml conc. |

Composition Containing Oleanoyl Peptide and Amla Extract for Enhanced UV B Protection Efficacy Swiss 3T3 mouse fibroblast cells were used for UV protection studies. The cells were seeded with a seeding density of 3000 cells per well of a 96 well plate. Confluent monolayers of Swiss 3T3 fibroblast cells were initially treated with varying concentrations of sample (composition containing Oleanoyl peptide and amla extract) and vehicle (control) in the culture medium and exposed to UV B irradiation of 0.036 J cm$^{-2}$ to determine the highest non cytotoxic concentration at which the sample provides maximum UV protection. 0.036 J cm$^{-2}$ was standardized as the UV dosage required for causing approximately 50% cell death to the cell cultures in the absence of protection. A control plate was also maintained under similar conditions without UV exposure which can only give observations on the cytotoxic potential of the sample. For each concentration, 6 replicates were maintained and the analysis was performed twice such that the 'n' value is 12. After UV exposure, the medium was replaced with fresh medium without sample and the cells were incubated in a $CO_2$ incubator for 48 hrs. The cells were then developed by NRU staining technique to analyze the cell viability. The cells were incubated with 0.003% solution of neutral red prepared in pre warmed DMEM medium for 3 hrs at 37° C. in $CO_2$ incubator. The excess dye was then washed off with phosphate buffer saline (PBS). The lysosomal dye was extracted in 100 µl of developer solution consisting of 25 ml of water, 24.5 ml of ethanol and 0.5 ml of glacial acetic acid at RT for 20 min. The optical density (OD) was read at 492 nm using a microplate reader.

The percentage reduction in UV induced cytotoxicity i.e., the percentage of UV protection was calculated with respect to the cytotoxicity in exposed cells as compared to that of the unexposed cells in the presence and absence of sample.

% UV induced cytotoxicity in cells without sample treatment $(U1)=[(C1-T1)/C1] \times 100$ C1=Absorbance due to cell viability in unexposed cells.
T1=Absorbance due to cell viability in UV exposed cells.

% UV induced cytotoxicity in sample treated cells $(U2)=[(C2-T2)/C2] \times 100$ C2=Absorbance due to cell viability in unexposed sample treated cells.
T2=Absorbance due to cell viability in UV exposed sample treated cells.

% UV protection=$[(U1-U2)/U1] \times 100$

U1=% UV induced cytotoxicity in cells without sample treatment.
U2=% UV induced cytotoxicity in samples treated cells.

The results in Table 7 and FIG. 14 shows that the composition containing Oleanoyl peptide and amla extract provides enhanced UV protection, thus indicating the composition is useful in protecting the skin from UV damage.

TABLE 7

| Product | % UV B protection |
| --- | --- |
| Amla extract | 53 ± 4% UV B protection as compared to untreated cells at 40 µg/ml conc. |
| Oleanoyl peptide | 13 ± 2.2% UV B protection as compared to untreated cells at 40 µg/ml conc. |
| Composition of amla extract & Oleanoyl peptide (1:1) | 80 ± 8% UV B protection as compared to untreated cells at 40 µg/ml conc. |

Composition Containing Oleanoyl Peptide and Stilbenes/Licorice Extract/Tetrahydrocurcuminoids (THC) for Enhanced Melanin Inhibition B16F1 mouse melanoma cells were seeded in a 6 well microtiter plate at a seeding density of 5000 cells per well in 2 ml DMEM medium per well. After 24 hours of incubation in a $CO_2$ incubator, melanin production is induced by 0.1 nM α-MSH by replacing the medium with medium containing α-MSH. The cells were then treated with varying concentrations of sample (composition containing oleanoyl peptide and stilbenes/licorice extract/THC) over a period of 9 days with renewal of α-MSH containing medium and sample at regular intervals of 3 days. Control wells were maintained without sample treatment and only with the vehicle used for sample preparation. After the incubation period, the medium was removed and the cells were scraped and washed in PBS. Thereafter, melanin was extracted by 1N NaOH in boiling water bath for 5 minutes. The absorbance of the melanin extract was read at 405 nm in a microplate reader. The inhibitory effect of the sample is calculated based on the decrease of melanin formation. The dose dependent inhibitory activity of samples is calculated and the results are expressed as $IC_{50}$ values using Graphpad prism software. The percentage of inhibition of melanin is calculated as follows, % Inhibition=$[(C-T)/C] \times 100$ Where C=absorbance due to melanin in the absence of inhibitor
T=absorbance due to melanin in the presence of inhibitor
$IC_{50}$ value is the concentration required for 50% inhibition of the melanin formation and hence, lower $IC_{50}$ value indicates better melanin inhibitory potential. It is clear from table 8 and FIG. 15 that the $IC_{50}$ values of compositions containing Oleanoyl peptide and stilbenes/licorice extract/THC are significantly lower than that of the individual active and hence provides enhanced activity.

TABLE 8

| | $IC_{50}$ (µg/ml) | |
| --- | --- | --- |
| Product | Individual active | In combination with Oleanoyl peptide (1:1) |
| Oleanoyl peptide | Not significant | |
| Resveratrol | 3.0 ± 0.2 | 1.6 ± 0.4 |
| Oxyresveratrol | 8.0 ± 1.2 | 4.3 ± 1.4 |
| Pterostilbene | 0.6 ± 0.1 | 0.34 ± 0.11 |
| 3Hydroxypterostilbene (3HPT) | 0.8 ± 0.22 | 0.42 ± 0.12 |
| Licorice extract | 3.0 ± 0.3 | 1.3 ± 0.4 |
| Tetrahydrocurcuminoids (THC) | 3.0 ± 0.2 | 1.2 ± 0.32 |

The sequence listing of peptides is included in the attached Appendix 1, and is also submitted via EFS Web as a file named sequencelistcip.txt.

---

We claim:
1. A method of elastase inhibition, said method comprising step of bringing into contact elastase enzyme and an effective amount of composition containing peptide of SEQ ID NO: 1 linked to oleanolic acid represented by structure I
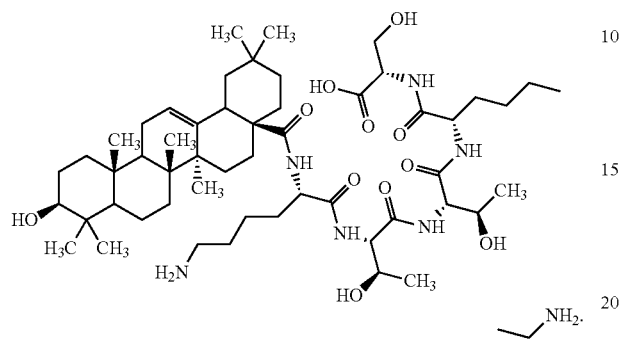
Structure I